United States Patent
Wang et al.

(10) Patent No.: US 9,719,857 B2
(45) Date of Patent: Aug. 1, 2017

(54) LASER INDUCED BREAKDOWN SPECTROSCOPY SAMPLE CHAMBER

(71) Applicant: THERMO SCIENTIFIC PORTABLE ANALYTICAL INSTRUMENTS INC., Tewksbury, MA (US)

(72) Inventors: Peidong Wang, Charlisle, MA (US); Haowen Li, Lexington, MA (US); Rong Sun, Winchester, MA (US); Michael Bush, Arlington, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 109 days.

(21) Appl. No.: 14/587,502

(22) Filed: Dec. 31, 2014

(65) Prior Publication Data

US 2016/0187201 A1 Jun. 30, 2016

(51) Int. Cl.
| | |
|---|---|
| *G01J 3/30* | (2006.01) |
| *G01J 3/443* | (2006.01) |
| *G01J 3/02* | (2006.01) |
| *G01N 21/15* | (2006.01) |
| *G01N 21/71* | (2006.01) |

(52) U.S. Cl.
CPC ............ *G01J 3/443* (2013.01); *G01J 3/0208* (2013.01); *G01J 3/0262* (2013.01); *G01N 21/15* (2013.01); *G01N 21/718* (2013.01)

(58) Field of Classification Search
CPC ........ G01J 3/443; G01J 3/0208; G01J 3/0267; G01J 3/0291; G01N 21/15; G01N 21/718
USPC ................................................ 356/318, 316
See application file for complete search history.

(56) References Cited

U.S. PATENT DOCUMENTS

| | | | |
|---|---|---|---|
| 4,191,475 | A | 3/1980 | Sourrouille |
| 6,233,307 | B1 | 5/2001 | Golenhofen |
| 7,834,999 | B2 | 11/2010 | Myrick et al. |

(Continued)

FOREIGN PATENT DOCUMENTS

| | | |
|---|---|---|
| CN | 103175808 | 6/2013 |
| CN | 203414408 | 1/2014 |

(Continued)

OTHER PUBLICATIONS

Nazarian, "Thermal and chemical kinetic characterization of multiphase and multicomponent substances by laser heating" International Journal of Heat and Mass Transfer, vol. 51, issues 5-6, Mar. 2008, pp. 1365-1378.

*Primary Examiner* — Hina F Ayub
(74) *Attorney, Agent, or Firm* — William R. McCarthy, III

(57) ABSTRACT

Methods and apparatus for laser induced breakdown spectroscopy (LIBS) sample chamber. An apparatus includes a sample chamber, a laser source connected to an excitation optics assembly, the excitation optics assembly connected to a first port on the sample chamber, a collimator assembly connected to a spectrometer, the collimator assembly connected to a second port on the sample chamber, and a first lens tube positioned on the first port and a second lens tube positioned on the second port, the first lens tube protecting the first port connected to the excitation optics assembly and the second lens tube protecting the second port connected to the collimator assembly from particles emitted when a laser pulse from the laser source ablates a surface of a target sample and generates a plasma.

26 Claims, 4 Drawing Sheets

(56) References Cited

U.S. PATENT DOCUMENTS

| | | |
|---|---|---|
| 8,319,964 B2 | 11/2012 | Hahn |
| 8,638,433 B1 | 1/2014 | Amend et al. |
| 2003/0234928 A1 | 12/2003 | Lucas et al. |
| 2004/0168631 A1 | 9/2004 | Honjou et al. |
| 2006/0096224 A1* | 5/2006 | Asbury .................. F16B 5/02 52/582.1 |
| 2006/0250614 A1* | 11/2006 | Plessers ............... C21C 5/4673 356/318 |
| 2012/0099103 A1 | 4/2012 | Hahn |
| 2012/0120395 A1 | 5/2012 | Hahn |
| 2013/0100444 A1 | 4/2013 | Chesner et al. |
| 2013/0208275 A1 | 8/2013 | Ikeda et al. |
| 2014/0202490 A1 | 7/2014 | Day |
| 2014/0204376 A1 | 7/2014 | Day |
| 2014/0268137 A1* | 9/2014 | Freda .................. G01J 3/0218 356/326 |
| 2016/0033328 A1* | 2/2016 | Walters ............... G01J 3/0264 356/327 |

FOREIGN PATENT DOCUMENTS

| | | |
|---|---|---|
| GB | 877918 A | 9/1961 |
| WO | 2013092981 | 6/2013 |

* cited by examiner

LASER INDUCED BREAKDOWN SPECTROSCOPY SAMPLE CHAMBER

BACKGROUND

The invention generally relates to spectroscopy, and more specifically to a laser induced breakdown spectroscopy (LIBS) sample chamber.

In general, laser induced breakdown spectroscopy (LIBS) is an emission spectroscopy technique where atoms and ions are primarily formed in their excited states as a result of interaction between a tightly focused laser beam and the material sample. The interaction between matter and high-density photons generates a plasma plume, which evolves with time and may eventually acquire thermodynamic equilibrium.

One of the important features of LIBS is that it does not require any sample preparation, unlike conventional spectroscopic analytical techniques. Samples in the form of solids, liquids, gels, gases, plasmas and biological materials can be studied with almost equal ease. LIBS has rapidly developed into a major analytical technology with the capability of detecting all chemical elements in a sample, of real-time response, and of close-contact or stand-off analysis of targets.

SUMMARY

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention provides methods and apparatus for a laser induced breakdown spectroscopy (LIBS) sample chamber.

In general, in one aspect, the invention features an apparatus including a sample chamber, a laser source connected to an excitation optics assembly, the excitation optics assembly connected to a first port on the sample chamber, a collimator assembly connected to a spectrometer, the collimator assembly connected to a second port on the sample chamber, and a first lens tube positioned on the first port and a second lens tube positioned on the second port, the first lens tube protecting the first port connected to the excitation optics assembly and the second lens tube protecting the second port connected to the collimator assembly from particles emitted when a laser pulse from the laser source ablates a surface of a target sample and generates a plasma.

In another aspect, the invention features an apparatus including a sample chamber, a laser source connected to an excitation optics assembly, the excitation optics assembly connected to a first port on the sample chamber, a collimator assembly connected to a spectrometer, the collimator assembly connected to a second port on the sample chamber, and a partition positioned between the first port and the target sample, the partition protecting the first port connected to the excitation optics assembly and the second port connected to the collimator assembly from particles emitted when a laser pulse from the laser source ablates a surface of a target sample and generates a plasma.

In another aspect, the invention features an apparatus including a sample chamber, a laser source connected to an excitation optics assembly, the excitation optics assembly connected to a first port on the sample chamber, an output end of a light pipe connected to a spectrometer, a collector end of the light pipe connected to the sample chamber, and a partition positioned between the first port and the target sample, the partition protecting the first port connected to the excitation optics assembly from particles emitted when a laser pulse from the laser source ablates a surface of a target sample and generates a plasma.

In another aspect, the invention features an apparatus including a sample chamber, a laser source connected to an excitation optics assembly, the excitation optics assembly connected to a first port on the sample chamber, a collimator assembly connected to a spectrometer, the collimator assembly connected to a second port on the sample chamber, and a lens tube positioned on the first or second port, the lens tube protecting the first port connected to the excitation optics assembly or the second port connected to the collimator assembly, from particles emitted when a laser pulse from the laser source ablates a surface of a target sample and generates a plasma.

The present invention may include one or more of the following advantages.

An apparatus includes a sample chamber in which one or more lens tubes protect the optics and/or the collimator assembly from damage and/or contamination in a laser induced breakdown spectroscopy (LIBS) system.

An apparatus includes a sample chamber in which a transparent material (e.g., quartz, glass or plastic) is appropriately fixated to protect the optics and/or collimator assembly from damage and/or contamination in a laser induced breakdown spectroscopy (LIBS) system.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The accompanying drawings, which are incorporated in and constitute a part of this specification, illustrate an embodiment of the invention and, together with a general description of the invention given above, and the detailed description of the embodiment given below, serve to explain the principles of the invention.

DETAILED DESCRIPTION

Figure 1:
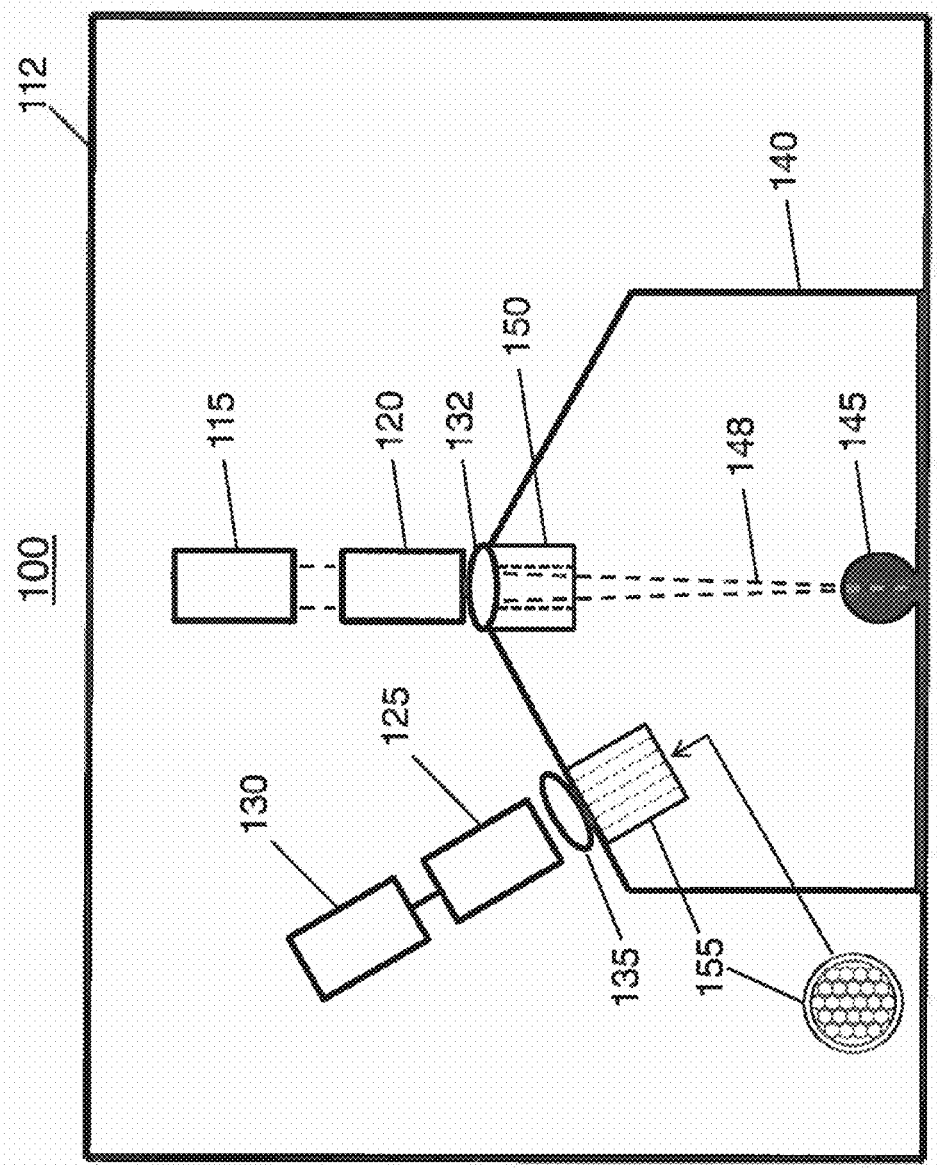
FIG. 1 is a block diagram of a first embodiment of an exemplary apparatus in accordance with the present invention.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As used herein, the term "or" is intended to mean an inclusive "or" rather than an exclusive "or." That is, unless specified otherwise, or clear from context, "X employs A or B" is intended to mean any of the natural inclusive permutations. That is, if X employs A, X employs B, or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As shown in FIG. 1, a first embodiment of an exemplary laser induced breakdown spectroscopy (LIBS) system 100 includes housing 112. The housing 112 includes laser source 115 connected to an excitation optics assembly 120. The housing 112 also includes a collimator assembly 125 connected to a spectrometer 130. The excitation optics assembly 120 and collimator assembly 125 are positioned on ports 132, 135, respectively, on a sample chamber 140. The sample chamber 140 includes a target sample 145. In some embodiments, LIBS system 100 is configured as a hand-held, self-contained analyzer as described in U.S. Pat. No. 8,355,126 B2, entitled: "HAND-HELD, SELF-CONTAINED OPTICAL EMISSION SPECTROSCOPY (OES) ANALYZER," issued to Goulter et al., and assigned to the assignees of the present application, the disclosure of which is hereby incorporated by reference in its entirety for all purposes. However, where anything in the incorporated reference contradicts anything stated in the present application, the present application prevails.

In operation, laser pulses 148 originated from the laser source 115 pass through the excitation optics assembly 120, which focuses the laser pulses 148 on a surface of the target sample 145. The laser pulses 148 generate a high temperature micro-plasma on the surface of the target sample 145. Particles, including atoms, molecules, and microscopic dust particles, are ablated from the surface of the target sample 145 into a plasma where they are atomized and energized. After this excitation, light that is characteristic of the elemental composition of the target sample 145 is emitted, collected by the collimator assembly 125 and analyzed within the spectrometer 130.

During operation, the particles that are ablated from the surface of the target sample 145 can reach the port 132 of the excitation optics assembly 120 and the port 135 of the collimator assembly 125, causing a particle build up on the port 132 and the port 135. If particle build up is allowed to occur, the effectiveness of the laser source 115 to ablate the surface of the target sample 145 and the collimator assembly 125 to receive light that is characteristic of the elemental composition of the target sample 145 is compromised.

To limit or reduce particle buildup, a first lens tube 150 is positioned over the port 132 of the excitation optics assembly 120 and a second lens tube 155 is positioned over the port 135 of the collimator assembly 125. In embodiments, the first lens tube 150 and second lens tube 155 may be baffled and/or constructed as a honeycomb, as shown in FIG. 1. In certain embodiments, the first lens tube 150 and second lens tube 155 extend into (e.g., partly into) the sample chamber 140, as shown in FIG. 1, or away from the sample chamber 140 (not shown). In still other embodiments, the first lens tube 150 and second lens tube 155 are removable for cleaning or replacement.

During operation, particles that are ablated from the surface of the target sample 145 are prevented from obstructing and/or damaging the excitation optics assembly 120 and collimator assembly 125 by the protection provided by the lens tube 150 and lens tube 155, respectively.

Figure 2:
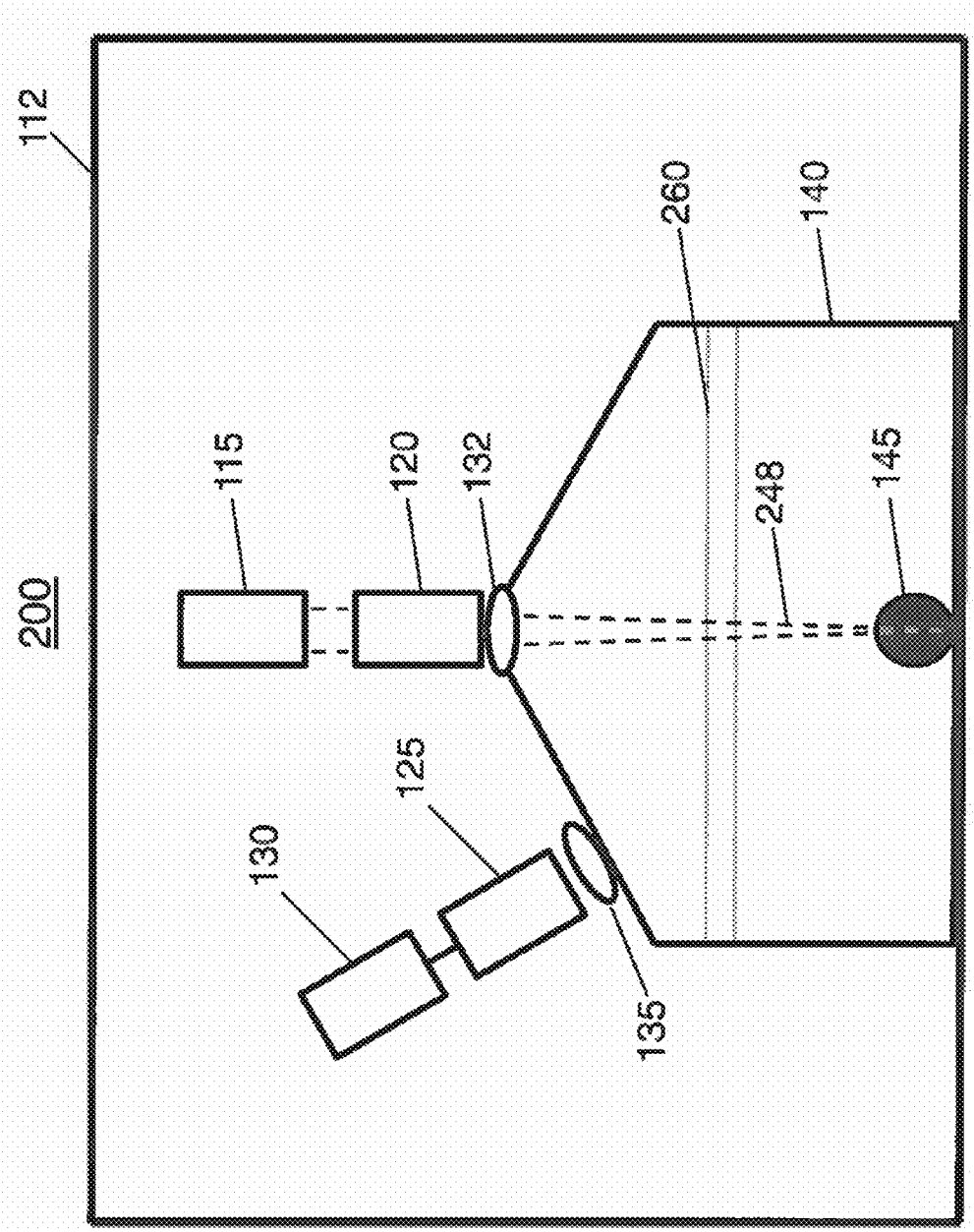
FIG. 2 is a block diagram of a second embodiment of an exemplary apparatus in accordance with the present invention.

As shown in FIG. 2, a second embodiment of an exemplary laser induced breakdown spectroscopy (LIBS) system 200 includes the housing 112. The housing 112 includes a laser source 115 connected to an excitation optics assembly 120. The housing 115 also includes a collimator assembly 225 connected to a spectrometer 130. The excitation optics assembly 120 and collimator assembly 225 are positioned on ports 132, 135, respectively, on a sample chamber 140. The sample chamber 140 includes a target sample 145.

In operation, laser pulses 248 originated from the laser source 115 pass through the excitation optics assembly 120, which focuses the laser pulses 248 on a surface of the target sample 145. The laser pulses 248 generate a high temperature micro-plasma on the surface of the target sample 145. Particles are ablated from the surface of the target sample 145 into a plasma where they are atomized and energized. After this excitation, light that is characteristic of the elemental composition of the target sample 145 is emitted, collected by the collimator assembly 225 and analyzed within the spectrometer 130.

During operation, the particles that are ablated from the surface of the target sample 145 can reach the port 132 of the excitation optics assembly 120 and the port 135 of the collimator assembly 225, causing a particle build up on the port 132 and the port 135. If particle build up is allowed to occur, the effectiveness of the laser source 115 to ablate the surface of the target sample 145 and the ability of the collimator assembly 125 to receive light that is characteristic of the elemental composition of the target sample 145 is compromised.

To prevent particle buildup, the sample chamber 140 includes a partition 260. The partition 260 is secured into the sidewall of the sample chamber 140 positioned between the target sample 145 and the ports 132, 135. In embodiments, the partition 260 is removable for cleaning or replacement. The partition 260 can be constructed of a transparent material (e.g., quartz, glass or plastic), that is, a material that is more than 90% optically transmissive at the wavelengths of interest.

During operation, particles that are ablated from the surface of the target sample 145 strike the partition 260 and thus are prevented from obscuring the ports 132, 135. More specifically, dust and particles are deposited on the partition 260. This insures that the excitation optics assembly 120 and collimator assembly 125 do not become contaminated and/or damaged by the particles.

Figure 3:
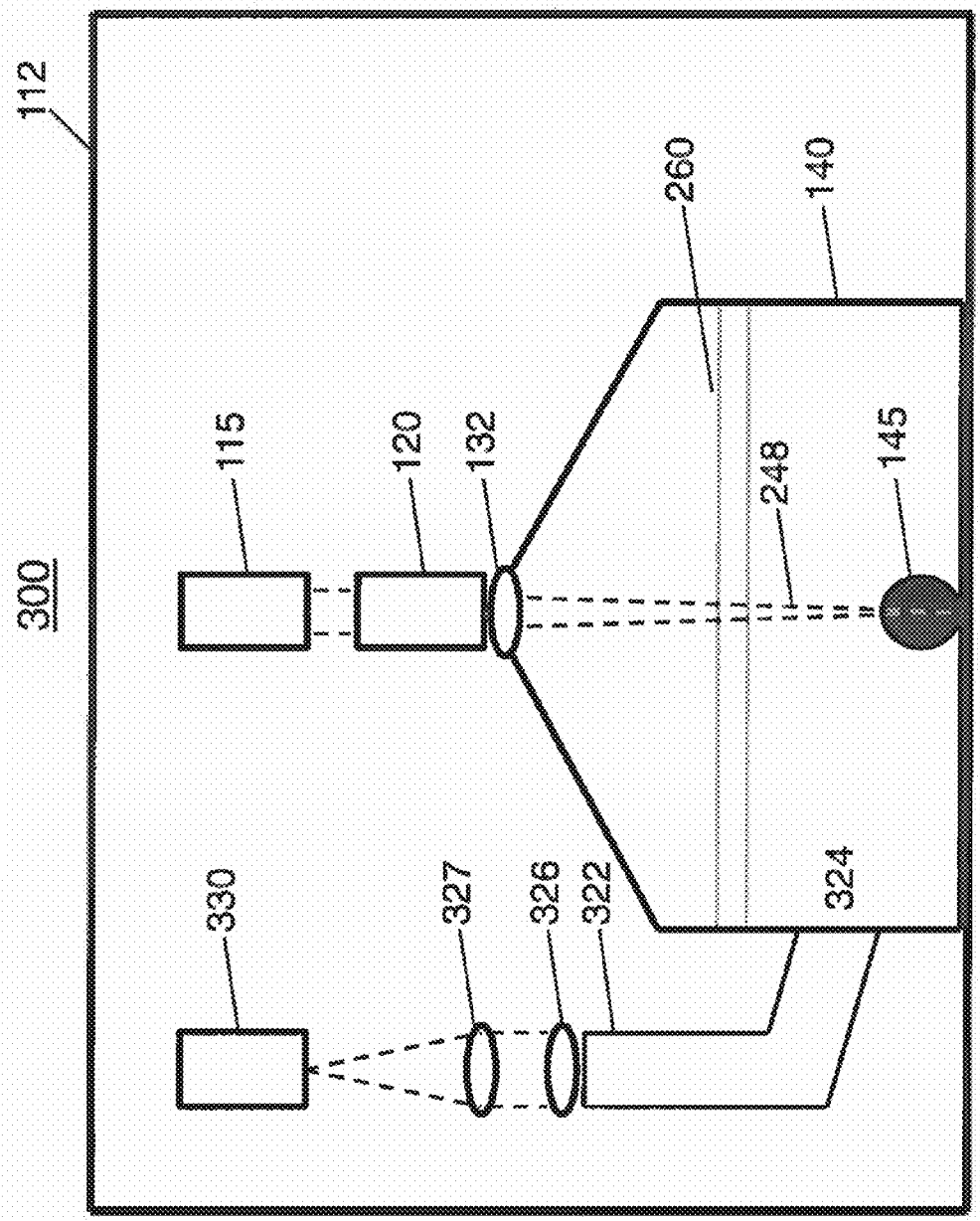
FIG. 3 is a block diagram of a third embodiment of an exemplary apparatus in accordance with the present invention.

As shown in FIG. 3, a third embodiment of an exemplary laser induced breakdown spectroscopy (LIBS) system 300 includes housing 112. The housing 112 includes laser source 115 connected to an excitation optics assembly 120. The housing 112 also includes a light pipe 322 connected to a spectrometer 330. In general, a light pipe is used to transfer light from one location to another. The light pipe 322 includes a collector end 324 and an output end 326. The light pipe 322, as shown in FIG. 3, is a hollow tube that includes a bend to prevent particle contamination, as described below. In one embodiment, the light pipe 322 is a hollow metal tube.

The excitation optics assembly 120 is positioned on a port 132 on a sample chamber 140 and the collector end 324 of the light pipe 322 is connected to the sample chamber 140. In one embodiment, the collector end 324 of the light pipe 322 is releasably coupled to the sample chamber 140 to aid in cleaning. The sample chamber 140 includes a target sample 145.

In operation, laser pulses 248 originated from the laser source 115 pass through the excitation optics assembly 120, which focuses the laser pulses 248 on a surface of the target sample 145. The laser pulses 248 generate a high temperature micro-plasma on the surface of the target sample 145. Particles are ablated from the surface of the target sample 145 into a plasma where they are atomized and energized. After this excitation, light that is characteristic of the elemental composition of the target sample 145 is emitted, collected by the light pipe 322, passed through a lens 327 and analyzed within the spectrometer 330.

During operation, the particles that are ablated from the surface of the target sample 145 can reach the port 132 of the excitation optics assembly 120 causing a particle build up on the port 132. If particle build up is allowed to occur, the effectiveness of the laser source 115 to ablate the surface of the target sample 145 and the ability of the light pipe 322 to receive light that is characteristic of the elemental composition of the target sample 145 is compromised.

To prevent particle buildup on port 132, the sample chamber 140 includes a partition 260. The partition 260 is secured into a sidewall of the sample chamber 240 and positioned between the target sample 145 and the port 132. In embodiments, the partition 260 is removable for cleaning or replacement. The partition 260 can be constructed of a transparent material (e.g., quartz, glass or plastic).

During operation, particles that are ablated from the surface of the target sample 145 strike the partition 260 and thus are prevented from obscuring the port 132. More specifically, dust and particles are deposited on the partition 260. This insures that the excitation optics assembly 120 does not become contaminated and/or damaged by the particles.

Figure 4:
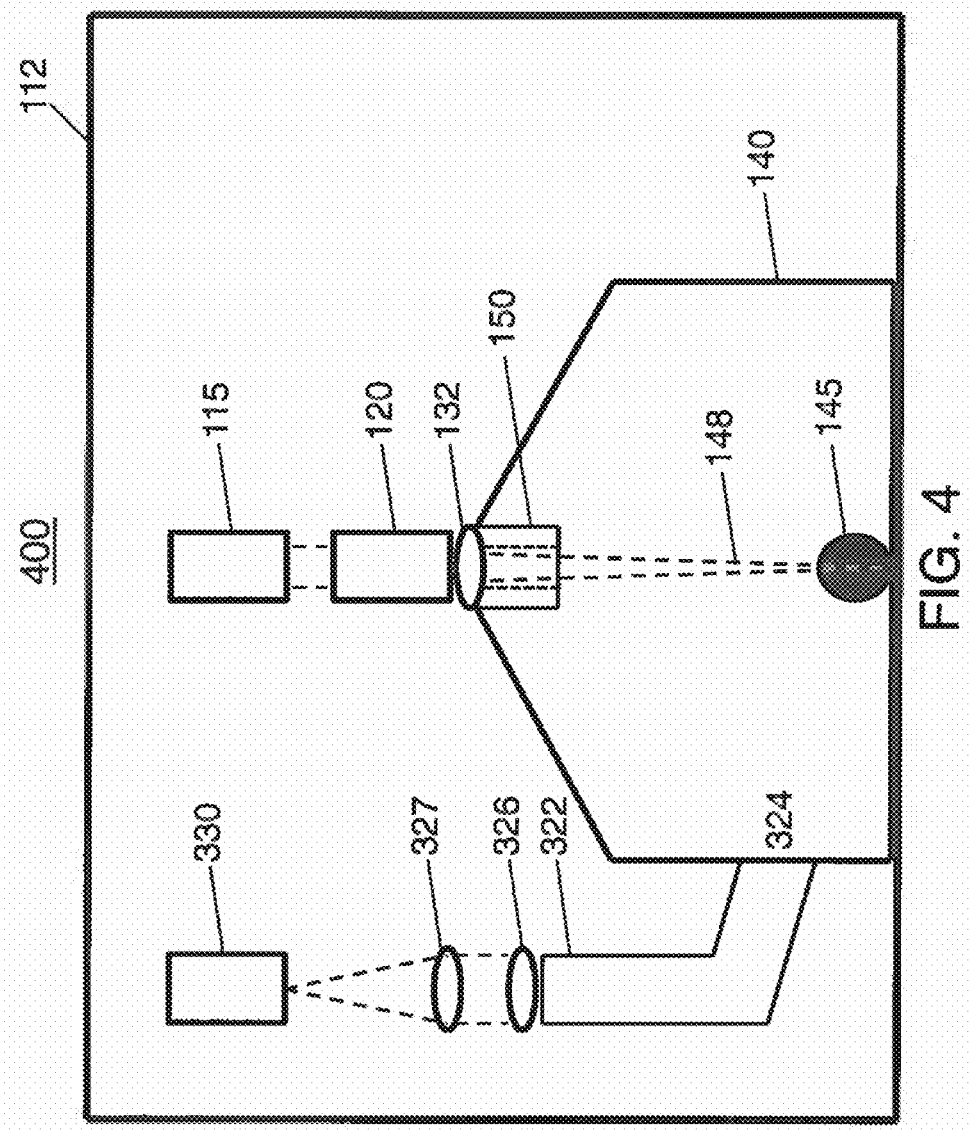
FIG. 4 is a block diagram of a fourth embodiment of an exemplary apparatus in accordance with the present invention.

In an alternate embodiment, as shown in FIG. 4 and described with reference to FIG. 1, the partition 260 in FIG. 3 may be eliminated in an exemplary laser induced breakdown spectroscopy (LIBS) system 400, and a lens tube 150 is positioned over port 132, or a lens tube 155 is positioned over port 135. In such a configuration, during operation, particles that are ablated from the surface of the target sample 145 are prevented from obstructing and/or damaging the excitation optics assembly 120 by the protection provided by the lens tube 150, or damaging the collimator assembly 125 by the protection provided by the lens tube 155. In certain embodiments, the lens tube 150 or the lens tube 155 extend into (e.g., partly into) the sample chamber 140, as shown in FIG. 1, or away from the sample chamber 140 (not shown). In one embodiment, as shown in FIG. 4, the collector end 324 of the light pipe 322 is connected to the sample chamber 140.

It is emphasized that the Abstract of the Disclosure is provided to comply with 37 C.F.R. Section 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

While the present invention has been illustrated by a description of an exemplary embodiment and while this embodiment has been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. An apparatus comprising:
   a sample chamber;
   a laser source connected to an excitation optics assembly, the excitation optics assembly connected to a first port on the sample chamber;
   a collimator assembly connected to a spectrometer, the collimator assembly connected to a second port on the sample chamber; and
   a first lens tube comprising an open end in the sample chamber and positioned on the first port and a second lens tube comprising an open end in the sample chamber and positioned on the second port, the first lens tube protecting the first port connected to the excitation optics assembly and the second lens tube protecting the second port connected to the collimator assembly from a build up of particles emitted when a laser pulse from the laser source ablates a surface of a target sample and generates a plasma.

2. The apparatus of claim 1 wherein the target sample is positioned in the sample chamber.

3. The apparatus of claim 1 wherein the spectrometer is a laser induced breakdown spectrometer.

4. The apparatus of claim 1 wherein the first lens tube and the second lens tube are constructed of a transparent material.

5. The apparatus of claim 4 wherein the transparent material is glass.

6. The apparatus of claim 4 wherein the transparent material is plastic.

7. The apparatus of claim 4 wherein the transparent material is honeycombed.

8. The apparatus of claim 1 wherein the first lens tube and the second lens tube are removable.

9. An apparatus comprising:
   a sample chamber;
   a laser source connected to an excitation optics assembly, the excitation optics assembly connected to a first port on the sample chamber;
   a collimator assembly connected to a spectrometer, the collimator assembly connected to a second port on the sample chamber; and
   a removable and optically transmissive partition secured into a sidewall of the sample chamber and positioned to physically separate the first port and the second port from a target sample, the removable and optically transmissive partition protecting the first port and the second port from a build up of particles emitted when a laser pulse from the laser source ablates a surface of the target sample and generates a plasma.

10. The apparatus of claim 9 wherein the target sample is positioned in the sample chamber.

11. The apparatus of claim 9 wherein the spectrometer is a laser induced breakdown spectrometer.

12. The apparatus of claim 9 wherein the removable and optically transmissive partition comprises a glass material.

13. The apparatus of claim 9 wherein the removable and optically transmissive partition comprises a plastic material.

14. An apparatus comprising:
a sample chamber;
a laser source connected to an excitation optics assembly, the excitation optics assembly connected to a first port on the sample chamber;
an output end of a light pipe connected to a spectrometer;
a collector end of the light pipe connected to the sample chamber, wherein the light pipe comprises a bend; and
a removable and optically transmissive partition secured into a sidewall of the sample chamber and positioned to physically separate the first port and a target sample, wherein the removable and optically transmissive partition protects the first port and the bend of the light pipe protects a lens from a build up of particles emitted when a laser pulse from the laser source ablates a surface of the target sample and generates a plasma.

15. The apparatus of claim 14 wherein the target sample is positioned in the sample chamber.

16. The apparatus of claim 14 wherein the spectrometer is a laser induced breakdown spectrometer.

17. The apparatus of claim 14 wherein the removable and optically transmissive partition comprises a glass material.

18. The apparatus of claim 14 wherein the removable and optically transmissive partition comprises a plastic material.

19. The apparatus of claim 14 wherein the light pipe is releasably connected to the sample chamber.

20. An apparatus comprising:
a sample chamber;
a laser source connected to an excitation optics assembly, the excitation optics assembly connected to a first port on the sample chamber;
a collimator assembly connected to a spectrometer, the collimator assembly connected to a second port on the sample chamber; and
a lens tube comprising an open end in the sample chamber and positioned on the first or second port, the lens tube protecting the first port connected to the excitation optics assembly or the second port connected to the collimator assembly, from a build up of particles emitted when a laser pulse from the laser source ablates a surface of a target sample and generates a plasma.

21. The apparatus of claim 20 further including an output end of a light pipe connected to a spectrometer, and a collector end of the light pipe connected to the sample chamber.

22. The apparatus of claim 20 wherein the lens tube is constructed of a transparent material.

23. The apparatus of claim 22 wherein the transparent material is glass.

24. The apparatus of claim 22 wherein the transparent material is plastic.

25. The apparatus of claim 22 wherein the transparent material is honeycombed.

26. The apparatus of claim 20 wherein the lens tube is removable.

* * * * *

UNITED STATES PATENT AND TRADEMARK OFFICE
CERTIFICATE OF CORRECTION

PATENT NO. : 9,719,857 B2
APPLICATION NO. : 14/587502
DATED : August 1, 2017
INVENTOR(S) : Peidong Wang et al.

It is certified that error appears in the above-identified patent and that said Letters Patent is hereby corrected as shown below:

On the Title Page

Column 1, item (72) Inventors: replace "Charlisle" with --Carlisle--.

Signed and Sealed this
Twenty-fourth Day of April, 2018

Andrei Iancu
*Director of the United States Patent and Trademark Office*